United States Patent [19]
Losel et al.

[11] 3,932,626
[45] Jan. 13, 1976

[54] PHARMACEUTICAL COMPOSITIONS CONTAINING A CARBOXYLIC ACYL DERIVATIVE OF DIGOXIN AND METHOD OF USE

[75] Inventors: Walter Losel; Herbert Merz, both of Ingelheim am Rhein; Wolfgang Hoefke, Budenheim; Werner Traunecker, Munster-Sarmsheim, all of Germany

[73] Assignee: Boehringer Ingelheim GmbH, Ingelheim am Rhein, Germany

[22] Filed: Jan. 16, 1974

[21] Appl. No.: 433,663

Related U.S. Application Data

[62] Division of Ser. No. 215,666, Jan. 5, 1972, Pat. No. 3,804,825.

[30] Foreign Application Priority Data
Jan. 14, 1971 Germany.............................. 2101595

[52] U.S. Cl.............................. 424/182; 260/210.5
[51] Int. Cl.².................................... A61K 31/705
[58] Field of Search................... 260/210.5; 424/182

[56] References Cited
UNITED STATES PATENTS
3,531,462 9/1970 Satoh et al........................ 260/210.5
3,696,091 10/1972 Eberlein et al. .................... 424/182

*Primary Examiner*—Lewis Gotts
*Assistant Examiner*—Cary Owens
*Attorney, Agent, or Firm*—Hammond & Littell

[57] ABSTRACT

Pharmaceutical dosage unit compositions containing as an active ingredient a compound of the formula

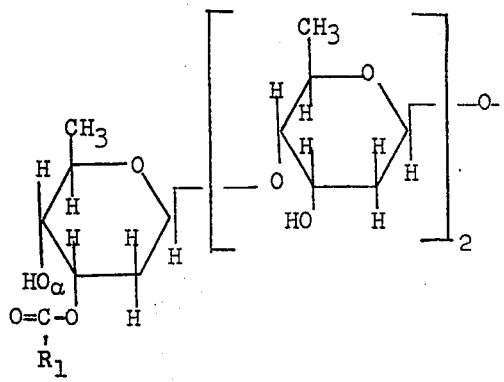

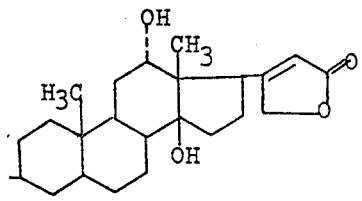

wherein $R_1$ is alkyl of 2 to 12 carbon atoms, halo-(alkyl of 1 to 4 carbon atoms), aryl-(alkyl of 1 to 4 carbon atoms), cycloalkyl-(alkyl of 1 to 4 carbon atoms) or cycloalkyl of 3 to 8 carbon atoms; and a method of using the same as cardiotonics.

13 Claims, No Drawings

PHARMACEUTICAL COMPOSITIONS CONTAINING A CARBOXYLIC ACYL DERIVATIVE OF DIGOXIN AND METHOD OF USE

This is a division of copending application Ser. No. 215,666, filed Jan. 5, 1972, now U.S. Pat. No. 3,804,825 issued Apr. 16, 1974.

This invention relates to novel pharmaceutical compositions containing as an active ingredient a carboxylic acyl derivative of digoxin, as well as to a method using the same as cardiotonics.

More particularly, the present invention relates to novel cardiotonic pharmaceutical dosage unit compositions containing as an active ingredient a carboxylic acyl derivative of digoxin represented by the formula

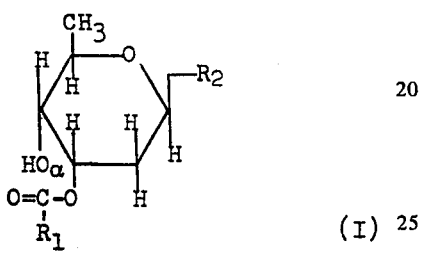

(I)

wherein $R_1$ is alkyl of 2 to 12 carbon atoms, halo-(alkyl of 1 to 4 carbon atoms), aryl-(alkyl of 1 to 4 carbon atoms), cycloalkyl-(alkyl of 1 to 4 carbon atoms) or cycloalkyl of 3 to 8 carbon atoms, and
$R_2$ is

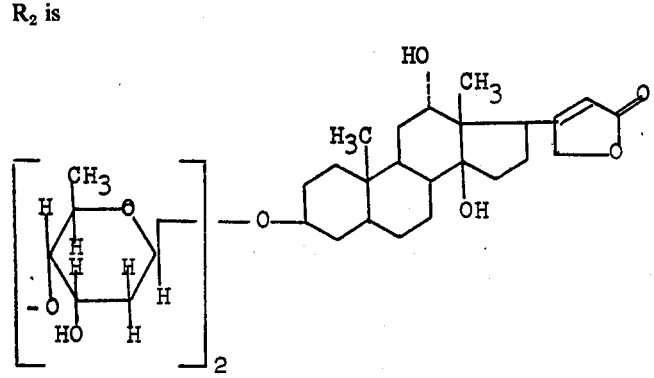

The compounds embraced by formula I may be prepared by the following methods:

METHOD A

By subjecting a glycoside of the formula

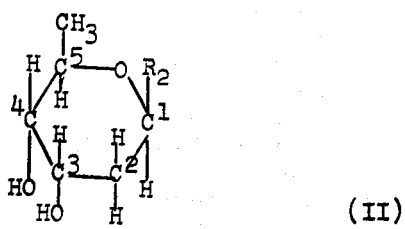

(II)

wherein $R_2$ has the same meanings as in formula I, to an ester exchange reaction with an ortho-ester of the formula $$R_1 - C(OR_3)_3 \quad (III)$$

wherein $R_1$ has the same meanings as in formula I and $R_3$ is lower alkyl, to form a cyclic ortho-ester of the formula

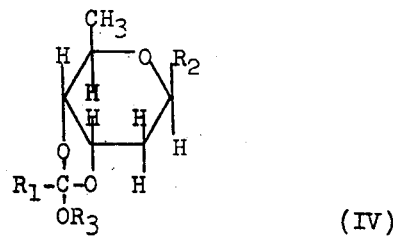

(IV)

wherein $R_1$, $R_2$ and $R_3$ have the meanings defined above, and subjecting the cyclic ortho-ester to a stereoselective partial hydrolysis reaction.

METHOD B

By reacting a glycoside of the formula II with an acylating agent of the formula $$R_1 - CO - X \quad (V)$$

wherein $R_1$ has the same meaning as in formula I and X is halogen, acyl or another anionically easily removable radical, and separating the desired monoacylated digitoxin derivative from the resulting mixture of isomeric monoacylated and polyacylated digitoxin derivatives pursuant to conventional methods.

The preparation of the cyclic ortho-ester of the formula IV by method A is carried out in the presence of an acid catalyst and, if desired, in the presence of an inert organic solvent, such as tetrahydrofuran, dioxane, chloroform or methylene chloride. Suitable acid catalysts are inorganic or strong organic acids, such as hydrohalic acids, sulfuric acid, p-toluenesulfonic acid, methanesulfonic acid or trichloroacetic acid; Lewis acids, such as potassium bisulfate, zinc chloride, boron-trifluoride-etherate or copper sulfate; or acid ion-exchangers, such as Amberlite IR 120 or Dowex 50.

The ester exchange reaction may be performed at a temperature between 0°C and the reflux temperature of the reaction mixture, but preferably at about room temperature.

The subsequent partial hydrolysis of the intermediate cyclic ortho-ester of the formula IV is carried out in the presence of an aqueous acid; if the intermediate ortho-ester has previously been isolated, it is redissolved in an inert organic solvent, such as ethyl acetate, prior to being subjected to partial hydrolysis.

We have found that it is particularly advantageous to admix the reaction mixture resulting from the ester exchange reaction with the aqueous acid and to perform the partial hydrolysis in situ therein. Any desired aqueous acid solution having a pH of 4 or less may be used. The hydrolysis reaction proceeds in stereo-selective fashion, that is, as a rule, the hydrolysis product consists uniformly of the derivative with an esterified OH-group in the 3'-position to the exclusion of all other theoretically possible derivatives.

The acylation of the free hydroxyl group in the $C^3$-position by method B may be effected according to any conventional acylation process, provided the stability of the starting compound of the formula II permits it. For example, it may be effected with a reactive derivative of the desired acid, such as an acyl halide, an acid anhydride or a mixed anhydride of an acid and a carbonic acid monoester, at room temperature in the presence of an inert solvent and an acid-binding agent. Suitable acid-binding agents are inorganic or tertiary organic bases; the latter, such as pyridine, may simultaneously serve as the solvent medium if they are provided in sufficient excess.

The reaction product obtained pursuant to method B consists predominantly of a mixture of α- and β-acyl-digoxin; it may be separated into its individual components and purified by conventional methods, such as by column chromatography, Craig-distribution chromatography and/or fractional crystallization. In order to increase the yield of the desired α-form, the undesired β-form may be isomerized in an inert solvent in the presence of an acid catalyst, preferably an acid adsorbent, such as active aluminum oxide.

The starting compound of the formula II is digoxin, which is a known compound [see The Merck Index, 8th Ed., page 365 (1968)].

The following examples illustrate the preparation of various compounds of the formula I.

EXAMPLE 1

α-Propionyl-digoxin by method B 3.22 gm of digoxin were dissolved in 75 ml of absolute pyridine, 0.6 ml of propionic acid anhydride (1.1 molar excess) was added to the solution, and the mixture was allowed to stand overnight at room temperature. Thereafter, the reaction mixture was poured into from 10 to 15 times its volume of water, the aqueous mixture was vacuum-filtered, and the filter cake was washed with water.

By extraction of the filtrate with chloroform, about 23% of non-acylated digoxin starting material was recovered.

The filter cake contained, in addition to residual amounts of digoxin, mainly the desired α-propionyl-digoxin, as well as β-propionyl-digoxin and a mixture of various higher acylated products. The glycoside mixture was worked up by repeated column chromatography on silicagel (grain size 0.05–0.2 mm), using as the elution agent chloroform to which increasing amounts (1–10%) of methanol were added.

The progress of the separation was followed on silica-gel plates, using a chloroform-methanol mixture (90:10) as the flow agent and a chloroformic 20% antimony trichloride solution as the revealing dye.

958 Mgm (27% of theory) of α-propionyl-digoxin, m.p. 175°–177°C after recrystallization from chloroform/methanol/ether (15:3:70), of the formula

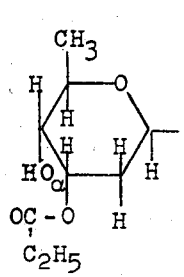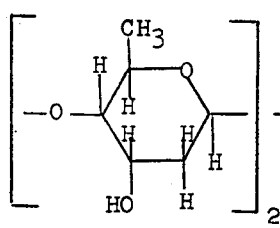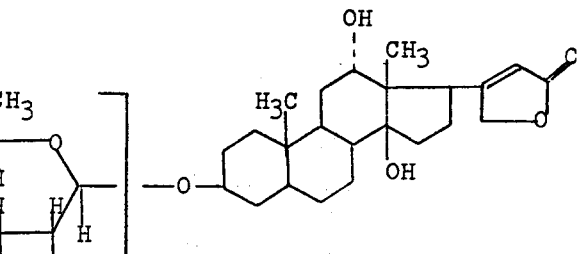

were obtained, and 916 mgm of digoxin were recovered.

EXAMPLE 2

α-Propionyl-digoxin by method A

A mixture consisting of 2 gm of digoxin, 100 ml of absolute tetrahydrofuran, 1 ml of ortho-propionic acid triethyl ester and 50 mgm of p-toluenesulfonic acid was stirred for 90 minutes at room temperature. Thereafter, in order to partially hydrolize the cyclic ortho-ester formed thereby, 50 mgm of p-toluenesulfonic acid and 2 ml of water were added to the reaction mixture. After completion of the acid hydrolysis, the reaction solution was neutralized by addition of triethylamine and then evaporated to dryness in vacuo on a water bath at 50°C. The residue was digested with water, the aqueous mixture was vacuum-filtered, and the filter cake was recrystallized from methanol/chloroform/ether (1:1:5), yielding 1.95 gm (about 91% of theory) of α-propionyl-digoxin having a melting point of 175°–179°C.

EXAMPLE 3

α-Butyryl-digoxin by method A

A mixture consisting of 2 gm of digoxin, 100 ml of absolute tetrahydrofuran, 1 ml of ortho-butyric acid triethyl ester and 50 mgm of p-toluenesulfonic acid was stirred for 90 minutes at room temperature. Thereafter, the reaction solution was neutralized with triethylamine, then evaporated to dryness in vacuo on a water bath at 50°C, and the residue was taken up in chloroform, and the resulting solution was briefly shaken with 20 ml of 0.1 N hydrochloric acid. The organic phase was separated, washed twice with water, dried over anhydrous sodium sulfate and evaporated to dryness in vacuo. The residue was recrystallized from chloroform/ether (1:5), yielding 1.90 gm (about 87% of theory) of α-butyryl-digoxin having a melting point of 186°–189°C.

EXAMPLE 4

Using a procedure analogous to that described in Example 1, 72% of theory of α-(chloro-acetyl)-digoxin, m.p. 190°–191°C, were obtained from ortho-chloroacetic acid triethyl ester and digoxin.

EXAMPLE 5

Using a procedure analogous to that described in Example 1, 88% of theory of α-(γ'-chloro-butyryl)-digoxin, m.p. 176°–179°C, were obtained from ortho-γ-chloro-butyric acid triethyl ester and digoxin.

EXAMPLE 6

Using a procedure analogous to that described in Example 1, 88% of theory of α-(cyclopropyl-carbonyl)-digoxin, m.p. 157°–160°C, were obtained from ortho-cyclopropanecarboxylic acid triethyl ester and digoxin.

EXAMPLE 7

Using a procedure analogous to that described in Example 1, 82% of theory of α-(cyclopentyl-carbonyl)-digoxin, m.p. 171°–173°C, were obtained from ortho-cyclopentanecarboxylic acid triethyl ester and digoxin.

EXAMPLE 8

Using a procedure analogous to that described in Example 1, 85% of theory of α-(cyclohexyl-carbonyl)-digoxin, m.p. 204°–206°C, were obtained from ortho-cyclohexanecarboxylic acid triethyl ester and digoxin.

EXAMPLE 9

Using a procedure analogous to that described in Example 1, 87% of theory of α-(cyclooctyl-carbonyl)-digoxin, m.p. 157°–158°C, were obtained from ortho-cyclooctanecarboxylic acid triethyl ester and digoxin.

EXAMPLE 10

Using a procedure analogous to that described in Example 1, 77% of theory of α-(cyclopentyl-acetyl)-digoxin, m.p. 202°C, were obtained from ortho-cyclopentylacetic acid triethyl ester and digoxin.

EXAMPLE 11

Using a procedure analogous to that described in Example 1, 83% of theory of α-(cyclohexyl-acetyl)-digoxin, m.p. 183°–186°C, were obtained from ortho-cyclohexylacetic acid triethyl ester and digoxin.

EXAMPLE 12

Using a procedure analogous to that described in Example 1, 87% of theory of α-(phenyl-acetyl)-digoxin, m.p. 145°–155°C, were obtained from ortho-phenylacetic acid triethyl ester and digoxin.

EXAMPLE 13

Using a procedure analogous to that described in Example 1, 93% of theory of α-(β'-phenyl-propionyl)-digoxin, m.p. 197°–199°C, were obtained from ortho-β-phenylpropionic acid triethyl ester and digoxin.

EXAMPLE 14

Using a procedure analogous to that described in Example 1, 85% of theory of α-(γ'-phenyl-butyryl)-digoxin, m.p. 163°–169°C, were obtained from ortho-γ-phenylbutyric acid triethyl ester and digoxin.

EXAMPLE 15

Using a procedure analogous to that described in Example 1, 73% of theory of α-lauroyl-digoxin, m.p. 190°–191°C, were obtained from ortho-lauric acid trimethyl ester and digoxin.

The compounds embraced by formula I above have useful pharmacodynamic properties. More particularly, they exhibit cardiotonic and especially positive inotropic activities in the isolated ventricle of the guinea pig heart as well as in the heart-lung preparation, and are therefore useful for the treatment of cardiac insufficiency in warmblooded animals. The cardiotonic activity of the compounds of the formula I is superior to and their toxicities significantly less than that of g-strophanthidin.

For pharmaceutical purposes the compounds of the formula I are administered to warm-blooded animals perorally, parenterally or rectally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective cardiotonic dosage unit of the compounds embraced by formula I is from 0.00083 to 0.084 mgm/kg body weight, preferably from 0.002 to 0.034 mgm/kg body weight.

The following examples illustrate a few pharmaceutical dosage unit compositions comprising a compound of the formula I as an active ingredient and represent the best modes contemplated of putting the invention into practical use. The parts are parts by weight unless otherwise specified.

EXAMPLE 16

Tablets

The tablet composition is compounded from the following ingredients:

| | | |
|---|---|---|
| α-(Chloro-acetyl)-digoxin | 0.25 | parts |
| Lactose | 85.75 | " |
| Potato starch | 30.0 | " |
| Gelatin | 3.0 | " |
| Magnesium stearate | 1.0 | " |
| Total | 120.0 | parts |

PREPARATION

The glycoside is intensively milled with ten times its weight of lactose, the milled mixture is admixed with the remaining amount of the lactose and the potato starch, the resulting mixture is moistened with an aqueous 10% solution of the gelatin, the moist mass is forced through a 1.5 mm-mesh screen, and the resulting granulate is dried at 40°C. The dry granulate is again passed through a 1 mm-mesh screen, admixed with the magnesium stearate, and the composition is compressed into 120 mgm-tablets in a conventional tablet making machine. Each tablet contains 0.25 mgm of the glycoside and is an oral dosage unit composition with effective cardiotonic action.

EXAMPLE 17

Coated pills

The pill core composition is compounded from the following ingredients:

| | | |
|---|---|---|
| α-Propionyl-digoxin | 0.25 | parts |
| Lactose | 32.25 | " |
| Corn starch | 15.00 | " |
| Polyvinylpyrrolidone | 2.00 | " |
| Magnesium stearate | 0.50 | " |
| Total | 50.0 | parts |

PREPARATION

The glycoside is intensively milled with ten times its weight of lactose, the milled mixture is admixed with the remainder of the lactose and the corn starch, the mixture is moistened with an aqueous 15% solution of the polyvinylpyrrolidone, the moist mass is forced through a 1 mm-mesh screen, and the resulting granulate is dried at 40°C and again passed through the screen. The dry granulate is admixed with the magnesium stearate, and the resulting composition is compressed into 50 mgm-pill cores which are subsequently coated in conventional manner with a thin shell consisting essentially of a mixture of sugar and talcum and finally polished with beeswax. Each coated pill contains 0.25 mgm of the glycoside and is an oral dosage unit composition with effective cardiotonic action.

EXAMPLE 18

Drop solution

The solution is compounded from the following ingredients:

| | | |
|---|---|---|
| α-(γ'-Chloro-butyryl)-digoxin | 0.0125 | parts |
| Saccharin sodium | 0.3 | " |
| Sorbic acid | 0.1 | " |
| Ethanol | 30.0 | " |
| Flavoring | 1.0 | " |
| Distilled water q.s.ad | 100.0 | " |

PREPARATION

The glycoside and the flavoring are dissolved in the ethanol, and the sorbic acid and the saccharin sodium are dissolved in the distilled water. The two solutions are uniformly admixed with each other, and the mixed solution is filtered until free from suspended matter. 1 ml of the filtrate contains 0.125 mgm of the glycoside and is an oral dosage unit composition with effective cardiotonic action.

EXAMPLE 19

Hypodermic solution

The solution is compounded from the following ingredients:

| | | |
|---|---|---|
| α-(γ'-Phenyl-butyryl)-digoxin | 0.25 | parts |
| Polyethyleneglycol 600 | 700.0 | " |
| Tartaric acid | 150.0 | " |
| Distilled water q.s.ad | 3000.0 | " |
| | | by vol. |

PREPARATION

The tartaric acid, the polyethyleneglycol and the glycoside are successively dissolved in a sufficient amount of distilled water, and the resulting solution is diluted with distilled water to the indicated volume and then filtered until free from suspended matter. The filtrate is filled into white 3 ml-ampules in an atmosphere of nitrogen, which are then sterilized for 20 minutes at 120°C and sealed. Each ampule contains 0.25 mgm of the glycoside, and the contents thereof are an injectable dosage unit composition with effective cardiotonic action.

EXAMPLE 20

Suppositories

The suppository composition is compounded from the following ingredients:

| | | |
|---|---|---|
| α-(Phenyl-acetyl)-digoxin | 0.25 | parts |
| Lactose | 4.75 | " |
| Suppository base (e.g. cocoa butter) | 1695.0 | " |
| Total | 1700.0 | parts |

PREPARATION

The glycoside and the lactose are admixed, and the mixture is milled. The milled mixture is uniformly stirred with the aid of an immersion homogenizer into the suppository base, which had previously been melted and cooleld to 40°C. The resulting composition is cooled to 37°C, and 1700 mgm-portions thereof are poured into cooled suppository molds and allowed to harden therein. Each suppository contains 0.25 mgm of the glycoside and is a rectal dosage unit composition with effective cardiotonic action.

Analogous results are obtained when any one of the other acylated digoxins embraced by formula I is substituted for the particular acylated digoxin in Examples 16 through 20. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A pharmaceutical dosage unit composition for increasing the strength of the heart muscle contraction in a warm-blooded animal, consisting essentially of an inert pharmaceutical carrier and an effective amount of a compound of the formula

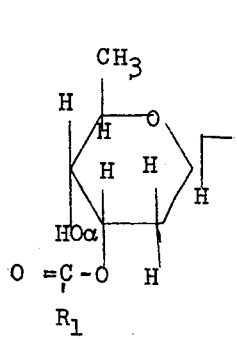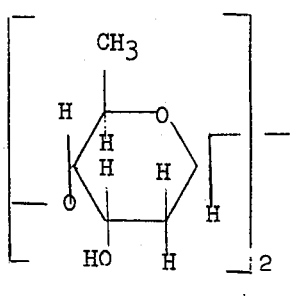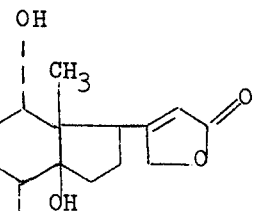

wherein $R_1$ is alkyl of 2 to 12 carbon atoms, chloro-(alkyl of 1 to 4 carbon atoms), phenyl-(alkyl of 1 to 4 carbon atoms), cycloalkyl of 5 to 6 carbon atoms(alkyl of 1 to 4 carbon atoms) or cycloalkyl of 3 to 8 carbon atoms.

2. A composition of claim 1, wherein $R_1$ is alkyl of 2 to 12 carbon atoms, chloro-(alkyl of 1 to 3 carbon atoms), phenyl-(alkyl of 1 to 3 carbon atoms), (cycloalkyl of 5 to 6 carbon atoms)-methyl or cycloalkyl of 3 to 8 carbon atoms.

3. A composition of claim 2, wherein said compound is α-(chloro-acetyl)-digoxin.

4. A composition of claim 2, wherein said compound is α-propionyl-digoxin.

5. A composition of claim 2, wherein said compound is α-butyryl-digoxin.

6. A composition of claim 2, wherein said compound is α-(γ'-chloro-butyryl)-digoxin.

7. A composition of claim 2, wherein said compound is α-(γ'-phenyl-butyryl)-digoxin.

8. A composition of claim 2, wherein said compound is α-(phenyl-acetyl)-digoxin.

9. A composition of claim 2, wherein said compound is α-(cyclopentyl-acetyl)-digoxin.

10. A composition of claim 2, wherein said compound is α-lauroyl-digoxin.

11. A composition of claim 2, wherein said compound is α-(cyclohexyl-carbonyl)-digoxin.

12. The method of increasing the strength of the heart muscle contraction in a warm-blooded animal in need of the same, which comprises administering to said animal an effective amount of a compound of the formula

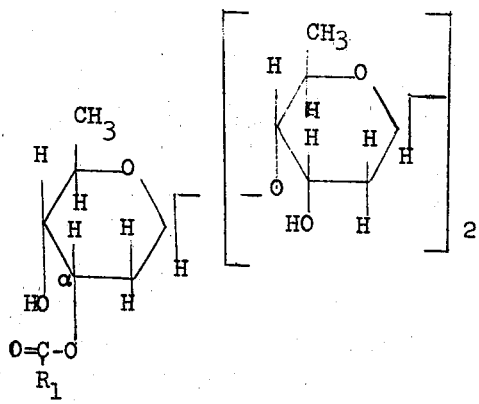

wherein $R_1$ is alkyl of 2 to 12 carbon atoms, chloro-(alkyl of 1 to 4 carbon atoms), phenyl-(alkyl of 1 to 4 carbon atoms), cycloalkyl of 5 to 6 carbon atoms-(alkyl of 1 to 4 carbon atoms) or cycloalkyl of 3 to 8 carbon atoms.

13. The method of claim 12, wherein $R_1$ is alkyl of 2 to 12 carbon atoms, chloro-(alkyl of 1 to 3 carbon atoms), phenyl-(alkyl of 1 to 3 carbon atoms), (cycloalkyl of 5 to 6 carbon atoms)-methyl or cycloalkyl of 3 to 8 carbon atoms.

* * * * *